(12) United States Patent
Miller

(10) Patent No.: US 8,968,803 B1
(45) Date of Patent: Mar. 3, 2015

(54) POWDERED TEAT DIP

(76) Inventor: Steven J. Miller, Hyrum, UT (US)

( * ) Notice: Subject to any disclaimer, the term of this patent is extended or adjusted under 35 U.S.C. 154(b) by 0 days.

(21) Appl. No.: 13/535,147

(22) Filed: Jun. 27, 2012

Related U.S. Application Data

(60) Provisional application No. 61/511,873, filed on Jul. 26, 2011.

(51) Int. Cl.
*A61K 36/30* (2006.01)
*A61K 36/185* (2006.01)

(52) U.S. Cl.
CPC ............................. *A61K 36/30* (2013.01)
USPC ................................................... 424/774

(58) Field of Classification Search
None
See application file for complete search history.

(56) References Cited

U.S. PATENT DOCUMENTS

| | | | |
|---|---|---|---|
| 4,668,692 A | 5/1987 | Noorlander et al. | |
| 5,578,312 A * | 11/1996 | Parrinello | 424/401 |
| 2010/0172848 A1* | 7/2010 | Modak et al. | 424/58 |

OTHER PUBLICATIONS

Website document entitled "Choosing the best teat dip for mastitis control and milk quality" (available at http://www.nmconline.org/articles/teatdip.htm). Downloaded from website Nov. 25, 2013.*
Website document entitled "Comfrey" (available at http://umm.edu/health/medical/altmed/herb/comfrey) Downloaded from website Nov. 26, 2013.*
Website document entitled "Kaolin" (available at http://www.ageless.co.za/kaolin.htm). Downloaded from website Nov. 26, 2013.*
Araujo et al. (2012) Pharmazie 67: 355-360.*
Grce et al. (2005) Microporous and Mesoporous Materials 79: 165-169.*
Zarkovic et al. (2003) Anticancer Res. 23: 1589-1596.*
Cerri et al. (2004) Applied Clay Science 27, 141-150.*
What is Zeolite (http://www.zeotechcorp.com/zeolite.asp), accessed Mar. 27, 2014.
Zeolite Applications (http://www.zeotechcorp.com/applications.asp), accessed Mar. 27, 2014.
ZeoMax Flow Agent Feed Additive (http://www.zeotechcorp.com/zeomaxfeed.asp), accessed Mar. 27, 2014.
ZeoMax Turf-Aid (http://www.zeotechcorp.com/zeomaxturf.asp), accessed Mar. 27, 2014.

* cited by examiner

*Primary Examiner* — Chris R Tate
*Assistant Examiner* — Russell Fiebig
(74) *Attorney, Agent, or Firm* — Warren M. Pate; Pate Peterson, PLLC

(57) ABSTRACT

A powdered teat dip for use on an organic dairy is disclosed. The powdered teat dip may include Chlorhexidine or Chlorhexidine Acetate at about 0.005 to about 2 percent by weight, Comfrey leaf powder at about 0.005 to about 2 percent by weight, and corn starch at about 40 to about 65 percent by weight.

1 Claim, 6 Drawing Sheets

Powdered Teat Dip 10c

Chlorhexidine or Chlorhexidine Acetate - 0.005 to 2 percent by weight

Comfrey Leaf Power - 0.005 to 2 percent by weight

ZEOMAX - 25 to 55 percent by weight

Sodium Erythorbate - 0.5 to 10 percent by weight

Ascorbic Acid - 0.005 to 2 percent by weight

Starch (e.g., Corn Starch) - 40 to 65 percent by weight

Kaolin - 2 to 12 percent by weight

Figure 11

POWDERED TEAT DIP

RELATED APPLICATIONS

This application claims the benefit of U.S. Provisional Patent Application Ser. No. 61/511,873 filed Jul. 26, 2011, which is hereby incorporated by reference.

BACKGROUND

1. The Field of the Invention

The invention relates to non-toxic, germicide, and healing compositions, and in particular, to such compositions which are adapted for topical application to dairy cattle and other domesticated farm animals.

2. The Background Art

The prevention of bovine mastitis is an important component of most dairy operations. One tool or method that has been used in such prevention is post-milking teat antisepses. This method typically involve dipping, after milking, teats of dairy animals with into appropriate germicidal preparation. The germicidal preparation may reduce teat skin colonization and contamination with mastitis-causing bacteria. It may also minimize penetration of mastitis-causing bacteria into the teat canal.

In the past, powdered teat dips have been used as post-milking, germicidal preparations. One such dip is disclosed in U.S. Pat. No. 4,668,692 issued May 26, 1987 to Noorlander et al., which is hereby incorporated by reference. Use of powdered teat dips is particularly helpful during extremely cold and windy weather. Under such conditions, the drying property of a powdered teat dip may remove surface moisture after milking. Accordingly, powdered teat dips may prevent chapping, cracking, frostbite, etc. as well as provide germicidal properties.

Current powdered teat dips have certain drawbacks. For example, they may not typically be used on dairy animals used in the product of "organic" milk. Accordingly, what is needed is an improved powdered teat dip that may be used on a greater percentage of dairy animals.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 11 is a schematic block diagram illustrating another embodiment of a powdered teat dip in accordance with the present invention.

DETAILED DESCRIPTION OF SELECTED EMBODIMENTS

Figure 1:
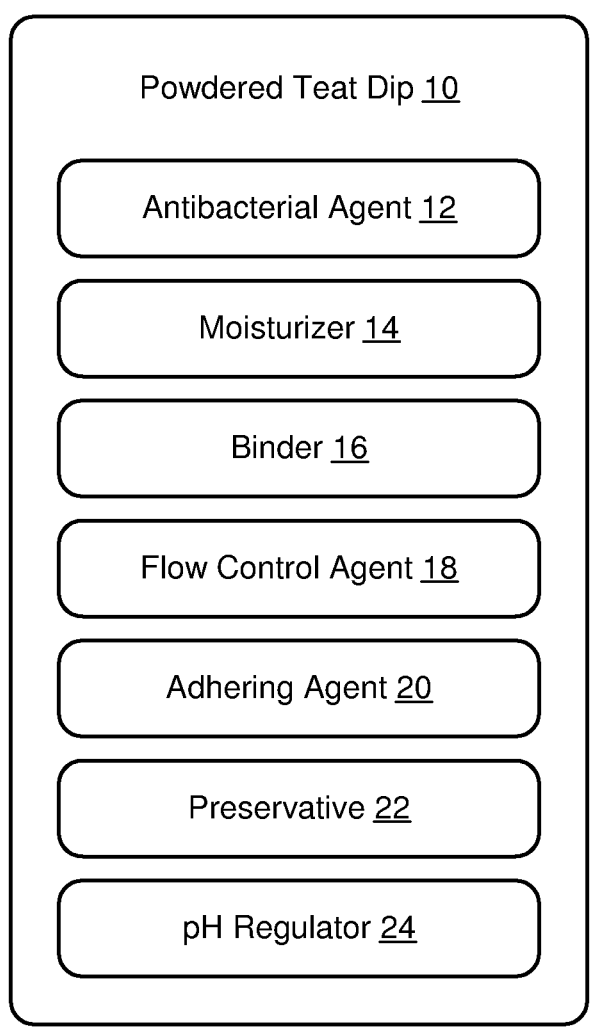
FIG. 1 is a schematic block diagram illustrating various roles that may be performed by the ingredients of a powdered teat dip in accordance with the present invention.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIG. 1, in selected embodiments, a powdered teat dip 10 in accordance with the present invention may be effective and advantageously used throughout the year. In the cold winter months, however, the composition may be particularly advantageous. A wet composition applied to the teats of cows during wet and cold conditions can cause chapping and frost damage. A dry composition may not have any such deleterious effect.

Each ingredient included within a powdered teat dip 10 in accordance with the present invention may perform at least one function or role. In selected embodiments, one or more ingredients within a powdered teat dip 10 may function as antibacterial agents 12, moisturizers 14, binders 16, flow control agents 18, adhering agents 20, preservatives 22, pH regulators 24, or the like. Certain ingredients may perform multiple roles. For example, a particular ingredient may function as both a binder 16 and as a flow control agent 18.

Not every role illustrated need be performed in all embodiments. For example, in selected embodiments, no preservation may be needed. Accordingly, in such embodiments, no ingredient that functions substantially exclusively as a preservative 22 need be included within the powdered teat dip 10. Additionally, a powdered teat dip 10 may include one or more ingredients that perform one or more functions or roles other than those illustrated.

Figure 2:
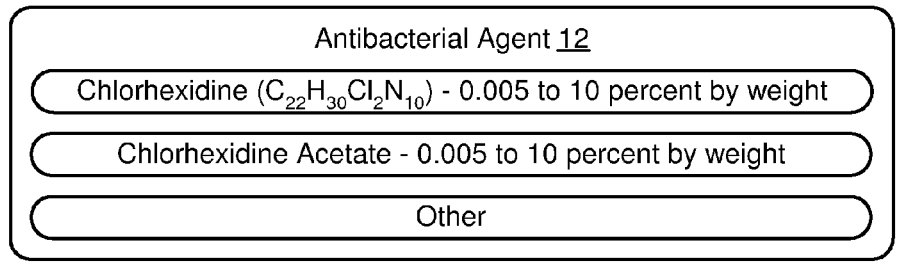
FIG. 2 is a schematic block diagram illustrating one or more ingredients that may individually, collectively, or semi-collectively operate in the role of antibacterial agent in a powdered teat dip in accordance with the present invention.

Referring to FIG. 2, in selected embodiments, a powdered teat dip 10 may include one or more ingredients that act as antibacterial agents 12. An antibacterial agent 12 may be an ingredient that is effective at killing or disabling infectious microorganisms (e.g., Staphylococcal bacteria, Streptococcal bacteria, and the like). The percentage by weight of any such ingredient or ingredients may be selected to provide the desired efficacy in role without excess (e.g., waste, adverse side effect, etc.). In selected embodiments, a powdered teat dip 10 may comprise an antibacterial agent 12 in the form of Chlorhexidine (e.g., Chlorhexidine Acetate) at about 0.005 to about 10 percent by weight.

Figure 3:
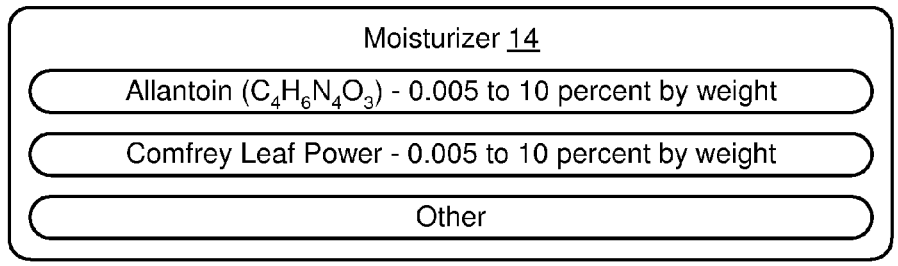
FIG. 3 is a schematic block diagram illustrating one or more ingredients that may individually, collectively, or semi-collectively operate in the role of moisturizer in a powdered teat dip in accordance with the present invention.

Referring to FIG. 3, in selected embodiments, a powdered teat dip 10 may include one or more ingredients that act as moisturizers 14. A moisturizer 14 may be an ingredient that is effective to make the external layers of teats softer and more pliable (e.g., by increasing hydration via reducing evaporation). The percentage by weight of any such ingredient or ingredients may be selected to provide the desired efficacy in role without excess. In selected embodiments, a powdered teat dip 10 may comprise a moisturizer 14 in the form of Allantoin at about 0.005 to about 10 percent by weight, Comfrey leaf powder at about 0.005 to about 10 percent by weight, or the like or combinations or sub-combinations thereof.

Figure 4:
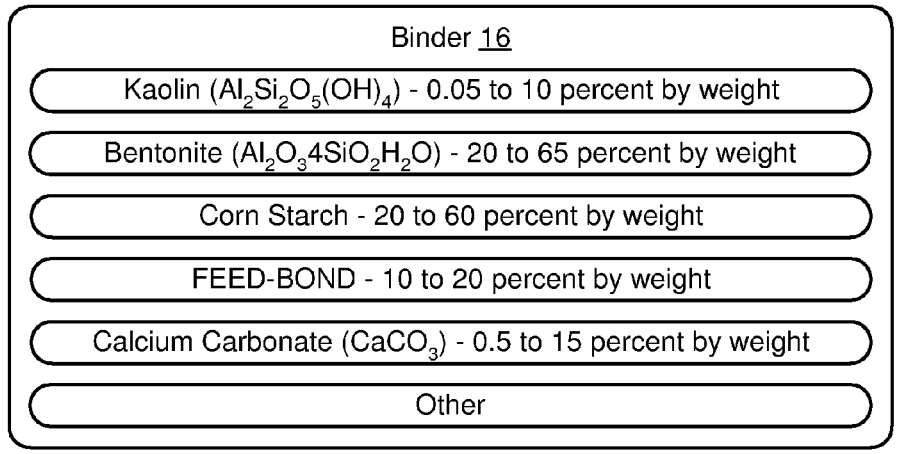
FIG. 4 is a schematic block diagram illustrating one or more ingredients that may individually, collectively, or semi-collectively operate in the role of binder in a powdered teat dip in accordance with the present invention.

Referring to FIG. 4, in selected embodiments, a powdered teat dip 10 may include one or more ingredients that act as binders 16. A binder 16 may be an ingredient that provides a suitable matrix into which the other ingredients of a powdered teat dip 10 may be distributed and held. The percentage by weight of any such ingredient or ingredients may be selected to provide the desired efficacy in role without excess. In selected embodiments, a powdered teat dip 10 may comprise a binder 16 in the form of Kaolin at about 0.05 to about 10 percent by weight, Bentonite at about 20 to about 60 percent by weight, corn starch at about 20 to about 60 percent by weight, FEED-BOND at about 10 to about 20 percent by weight, Calcium Carbonate at about 0.5 to about 15 percent by weight, or the like or combinations or sub-combinations thereof.

Figure 5:
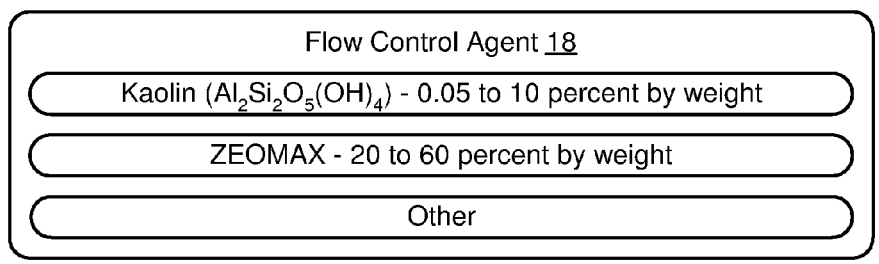
FIG. 5 is a schematic block diagram illustrating one or more ingredients that may individually, collectively, or semi-collectively operate in the role of flow control agent in a powdered teat dip in accordance with the present invention.

Referring to FIG. 5, in selected embodiments, a powdered teat dip 10 may include one or more ingredients that act as flow control agents 18. A flow control agent 18 may be an ingredient that is effective at increasing the ability of a powdered teat dip 10 to flow (e.g., pour, move, dip) in a smooth, liquid-like manner. The percentage by weight of any such ingredient or ingredients may be selected to provide the desired efficacy in role without excess. In selected embodiments, a powdered teat dip 10 may comprise a flow control agent 18 in the form of Kaolin at about 0.05 to about 10 percent by weight, ZEOMAX (i.e., clinoptilolite zeolite) at about 20 to about 60 percent by weight, or the like or combinations or sub-combinations thereof.

Figure 6:
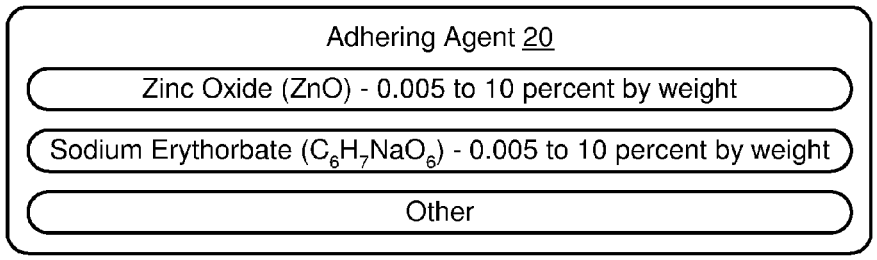
FIG. 6 is a schematic block diagram illustrating one or more ingredients that may individually, collectively, or semi-collectively operate in the role of adhering agent in a powdered teat dip in accordance with the present invention.

Referring to FIG. 6, in selected embodiments, a powdered teat dip 10 may include one or more ingredients that act as adhering agents 20. An adhering agent 20 may be an ingredient that is effective at increasing the ability of a powdered teat dip 10 to adhere to a teat during a post-milking application process. The percentage by weight of any such ingredient or ingredients may be selected to provide the desired efficacy in role without excess. In selected embodiments, a powdered teat dip 10 may comprise an adhering agent 20 in the form of Zinc Oxide at about 0.005 to about 10 percent by weight, Sodium Erythorbate at about 0.005 to about 10 percent by weight, or the like or combinations or sub-combinations thereof.

Figure 7:
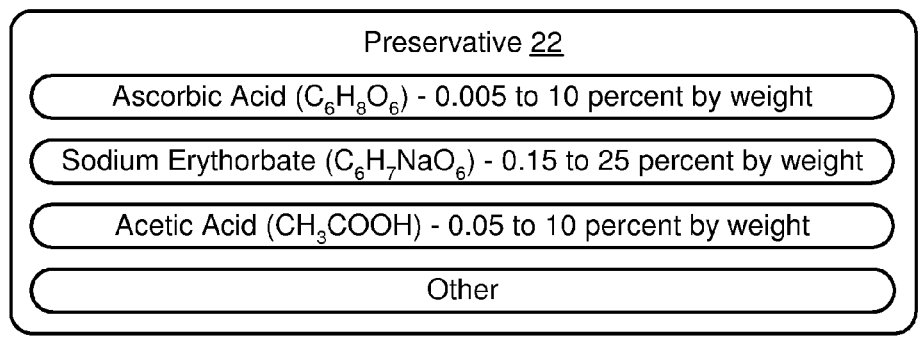
FIG. 7 is a schematic block diagram illustrating one or more ingredients that may individually, collectively, or semi-collectively operate in the role of preservative in a powdered teat dip in accordance with the present invention.

Referring to FIG. 7, in selected embodiments, a powdered teat dip 10 may include one or more ingredients that act as preservatives 22. A preservative 22 may be an ingredient that is effective at increasing the "shelf life" of a powdered teat dip 10. The percentage by weight of any such ingredient or ingredients may be selected to provide the desired efficacy in role without excess. In selected embodiments, a powdered teat dip 10 may comprise a preservative 22 in the form of Ascorbic Acid at about 0.005 to about 10 percent by weight, Sodium Erythorbate at about 0.15 to about 25 percent by weight, Acetic Acid at about 0.05 to about 10 percent by weight, or the like or combinations or sub-combinations thereof.

Figure 8:
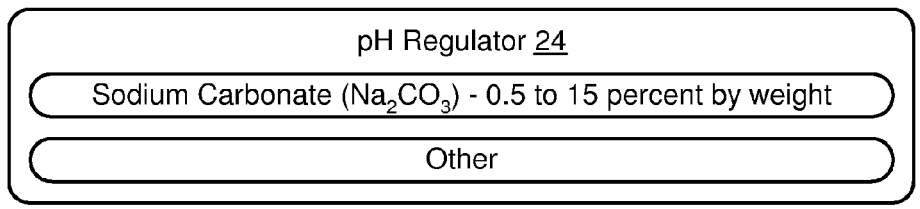
FIG. 8 is a schematic block diagram illustrating one or more ingredients that may individually, collectively, or semi-collectively operate in the role of pH regulator in a powdered teat dip in accordance with the present invention.

Referring to FIG. 8, in selected embodiments, a powdered teat dip 10 may include one or more ingredients that act as pH regulators 24. A pH regulator 24 may be an ingredient that is effective at maintaining the pH of a powdered teat dip 10 or an exterior surface of a teat treated therewith within a desired range. The percentage by weight of any such ingredient or ingredients may be selected to provide the desired efficacy in role without excess. In selected embodiments, a powdered teat dip 10 may comprise a pH regulator 24 in the form of Sodium Carbonate at about 0.5 to about 15 percent by weight.

Figure 9:
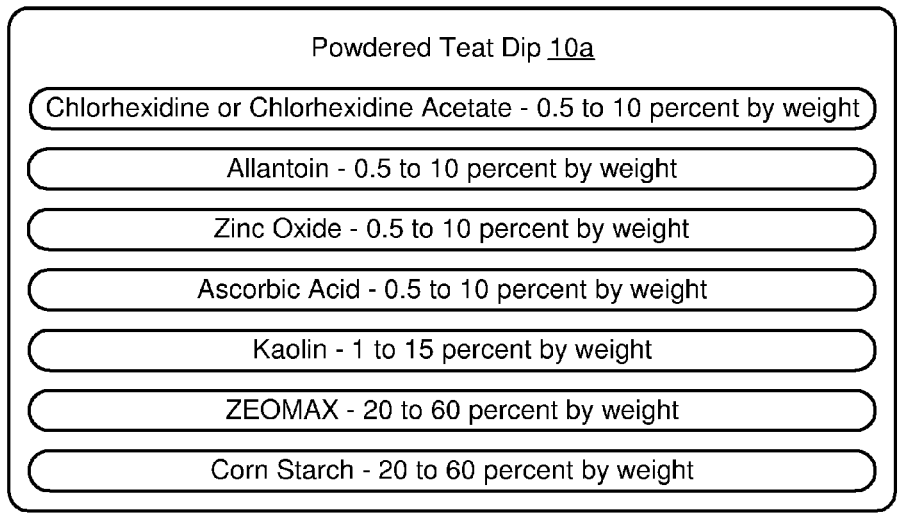
FIG. 9 is a schematic block diagram illustrating one embodiment of a powdered teat dip in accordance with the present invention.

Referring to FIG. 9, for selected applications (e.g., use on an "organic" dairy), one presently preferred powdered teat dip 10a comprises Chlorhexidine or Chlorhexidine Acetate at about 0.5 to about 10 percent by weight, Allantoin at about 0.5 to about 10 percent by weight, Zinc Oxide at about 0.5 to about 10 percent by weight, Ascorbic Acid at about 0.5 to about 10 percent by weight, Kaolin at about 1 to about 15 percent by weight, ZEOMAX at about 20 to about 60 percent by weight, and corn starch at about 20 to about 60 percent by weight.

Figure 10:
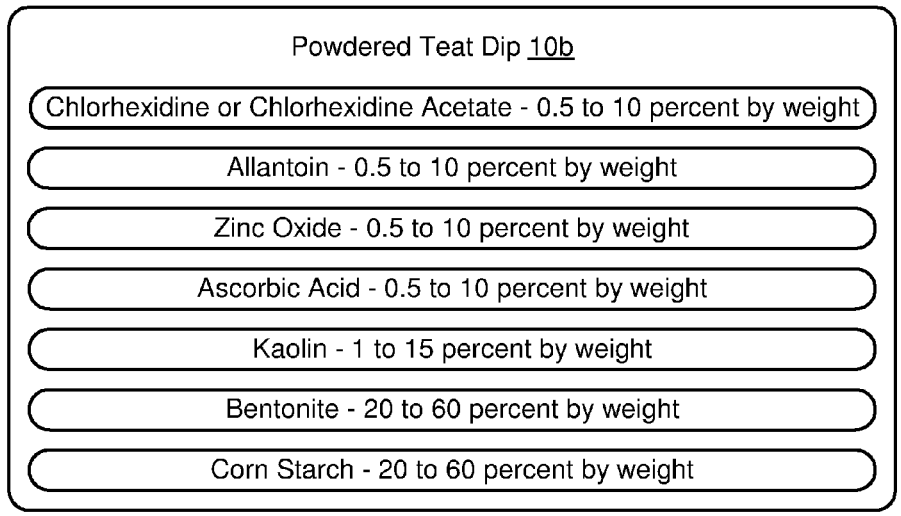
FIG. 10 is a schematic block diagram illustrating another embodiment of a powdered teat dip in accordance with the present invention.

Referring to FIG. 10, for selected applications (e.g., use on an "organic" dairy), another presently preferred powdered teat dip 10b comprises Chlorhexidine or Chlorhexidine Acetate at about 0.5 to about 10 percent by weight, Allantoin at about 0.5 to about 10 percent by weight, Zinc Oxide at about 0.5 to about 10 percent by weight, Ascorbic Acid at about 0.5 to about 10 percent by weight, Kaolin at about 1 to about 15 percent by weight, Bentonite at about 20 to about 60 percent by weight, and corn starch at about 20 to about 60 percent by weight.

Referring to FIG. 11, for selected applications (e.g., use on an "organic" dairy), another presently preferred powdered teat dip 10c comprises Chlorhexidine or Chlorhexidine Acetate at about 0.005 to about 2 percent by weight, Comfrey leaf powder at about 0.005 to about 2 percent by weight, ZEOMAX at about 25 to about 55 percent by weight, Sodium Erythorbate at about 0.5 to about 10 percent by weight, Ascorbic Acid at about 0.005 to about 2 percent by weight, starch (e.g., corn starch) at about 40 to about 65 percent by weight, and Kaolin at about 2 to about 12 percent by weight.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method of germicidally-treating teats of a dairy animal comprising the sequential steps of:
   (1) selecting a dairy animal having at least one teat;
   (2) completing a milking session of the animal;
   (3) dipping the at least one teat into a powdered teat dip composition;
   wherein the powdered teat dip composition comprises:
   0.005 to 2 wt % chlorhexidine or chlorhexidine acetate,
   0.005 to 2 wt % comfrey leaf powder, 20 to 60 wt % clinoptilolite zeolite,
0.5 to 10% wt % sodium erythrobate,
0.005 to 2 wt % ascorbic acid,
40-65 wt % corn starch, and
2-12 wt % kaolin.

\* \* \* \* \*